US008658618B2

(12) United States Patent
Spector

(10) Patent No.: US 8,658,618 B2
(45) Date of Patent: Feb. 25, 2014

(54) METHODS FOR PREVENTING OR REDUCING NEUROTOXICITY ASSOCIATED WITH ADMINISTERING DPD INHIBITORS IN COMBINATION WITH 5-FU AND 5-FU PRODRUGS

(75) Inventor: Thomas Spector, Durham, NC (US)

(73) Assignee: Adherex Technologies, Inc., Durham, NC (US)

( * ) Notice: Subject to any disclaimer, the term of this patent is extended or adjusted under 35 U.S.C. 154(b) by 56 days.

(21) Appl. No.: 12/904,974

(22) Filed: Oct. 14, 2010

(65) Prior Publication Data

US 2011/0130359 A1 Jun. 2, 2011

Related U.S. Application Data

(60) Provisional application No. 61/251,449, filed on Oct. 14, 2009.

(51) Int. Cl.
*A61K 31/70* (2006.01)
*A61K 31/505* (2006.01)

(52) U.S. Cl.
USPC .............................. 514/50; 514/256; 514/274

(58) Field of Classification Search
USPC ...................... 514/274, 256, 49, 50
See application file for complete search history.

(56) References Cited

U.S. PATENT DOCUMENTS

| | | | |
|---|---|---|---|
| 5,476,855 A | 12/1995 | El Kouni et al. | |
| 5,817,664 A * | 10/1998 | Spector et al. | 514/274 |
| 6,114,520 A | 9/2000 | Hattori et al. | |
| 6,177,436 B1 | 1/2001 | Spector et al. | |
| 2004/0028687 A1 | 2/2004 | Waelti | |
| 2006/0148753 A1 | 7/2006 | Spector et al. | |
| 2007/0232529 A1 | 10/2007 | Mickle et al. | |

FOREIGN PATENT DOCUMENTS

| | | |
|---|---|---|
| EP | 272065 | 4/1993 |
| EP | 356166 | 4/1994 |
| WO | 9204901 | 4/1992 |
| WO | 9512400 | 5/1995 |
| WO | 2006060697 | 6/2006 |

OTHER PUBLICATIONS

Ansfield et al., "A phase III study comparing the clinical utility of four regimens of 5-fluorouracil", Cancer, 1977, vol. 39, pp. 34-40.
Baker et al., "Phase I and pharmacologic study of oral fluorouracil on a chronic daily schedule in combination with the dihydropyrimidine dehydrogenase inactivator eniluracil", Journal of Clinical Oncology, 2000, vol. 18, pp. 915-926.
Barr et al., "Incorporation of 5-substituted uracil derivatives into nucleic acids. Part IV. The synthesis of 5-ethynyluracil", Nucleic Acids Research, 1976, vol. 3, pp. 2845-2849.
Barr et al., "Synthesis of some 5-halogenovinyl derivatives of uracil and their conversion into 2'-deoxyribonucleosides", Perkin Transactions, vol. 1, 1981, pp. 1665-1670.
Bleackley et al., "5-cyanouracil and 5-[14C]cyanouracil", Nucleic Acid Chemistry, Improved and New Synthetic Procedures, Methods and Techniques, Part 2, Townsend, L.B. et al. (eds.), John Wiley & Sons, New York, 1978, pp. 927-930.
Cao et al., "5-Ethynyluracil (776C85): Modulation of 5-fluorouracil efficacy and therapeutic index in rats bearing advanced colorectal carcinoma", Cancer Research, 1994, vol. 54, pp. 1507-1510.
Cao et al., "Alpha-fluoro-beta-alanine: Effects on the antitumor activity and toxicity of 5-fluorouracil", Biochemical Pharmacology, 2000, vol. 59, pp. 953-960.
Chabner et al., "Clinical pharmacology of cancer chemotherapy", Cancer Principles and Practice of Oncology, 2nd Edition, 1985, pp. 287-328.
Christophidis et al., "Fluorouracil therapy in patients with carcinoma of the large bowel: A pharmacokinetic comparison of various rates and routes of administration", Clinical Pharmacokinetics, 1978, vol. 3, pp. 330-336.
Cohen et al., "Clinical pharmacology of oral and intravenous 5-fluorouracil (NSC-19893)", Cancer Chemotherapy Reports, Part I, 1974, vol. 58, pp. 723-731.
Daher et al., "Metabolism of pyrimidine analogues and their nucleosides", Pharmacology & Therapeutics, 1990, vol. 48, pp. 189-222.
Etienne et al., "Response to fluorouracil therapy in cancer patients: The role of tumoral dihydropyrimidine dehydrogenase activity", Journal of Clinical Oncology, 1995, vol. 13, pp. 1663-1670.
Finch et al., "Plasma levels of 5-fluorouracil after oral and intravenous administration in cancer patients", British Journal of Clinical Pharmacology, 1979, vol. 7, pp. 613-617.
Fischel et al., "Dihydropyrimidine dehydrogenase: A tumoral target for fluorouracil modulation", Clinical Cancer Research, vol. 1, 1995, pp. 991-996.
Fischel et al., "Dual modulation of 5-fluorouracil cytotoxicity using folinic acid with dihydropyrimidine dehydrogenase inhibitor", Biochemical Pharmacology, 1997, vol. 53, pp. 1703-1709.
Fleming et al., "Correlation between dihydropyrimidine dehydrogenase activity in peripheral mononuclear cells and systemic clearance of fluorouracil in cancer patients", Cancer Research, 1992, vol. 52, pp. 2899-2902.
Grem et al., "Inter- and intraindividual variation in dihydropyrimidine dehydrogenase activity in peripheral blood mononuclear cells", Cancer Chemotherapy and Pharmacology, 1997, vol. 40, pp. 117-125.
Grem et al., "Overview of current status and future direction of clinical trials with 5-fluorouracil in combination with folinic acid", Cancer Treatment Reports, 1987, vol. 71, pp. 1249-1264.

(Continued)

*Primary Examiner* — Elli Peselev
(74) *Attorney, Agent, or Firm* — Klauber & Jackson LLC

(57) ABSTRACT

Methods for improved administration and dosing of DPD inhibitors in combination with 5-FU and/or 5-FU prodrugs are provided, comprising first administering to a patient in need thereof a DPD inhibitor that substantially eliminates activity of the enzyme in both nervous and non-nervous tissues within the patient and thereafter administering 5-FU or a 5-FU prodrug, wherein the level of 5-FU or 5-FU generated from a prodrug is in substantial excess of DPD inhibitor in the patient.

40 Claims, 3 Drawing Sheets

(56) References Cited

OTHER PUBLICATIONS

Guo et al., "Pharmacokinetic and pharmacodynamic effects of oral eniluracil fluorouracil and leucovorin given on a weekly schedule", Cancer Chemotherapy & Pharmacology, 2003, vol. 52, pp. 79-85.
Hein et al., "Uber die darstellung von 5-trifluormethyluracil", Zeitschrift Fur Chemie, 1977, vol. 17, pp. 415-416.
Ho et al., "Distribution and inhibition of dihydrouracil dehydrogenase activities in human tissues using 5-fluorouracil as a substrate", Anticancer Research, 1986, vol. 6, pp. 781-784.
Hohneker et al., "Clinical development of eniluracil: Current status", Oncology, 1998, vol. 12 (10 Suppl. 7), pp. 52-56.
Jones et al., "A method for the rapid preparation of 5-vinyluracil in high yield", Nucleic Acids Research, 1974, vol. 1, pp. 105-107.
Keith et al., "Impact of two weekly schedules of oral eniluracil given with fluorouracil and leucovorin on the duration of dihydropyrimidine dehydrogenase inhibition", Clinical Cancer Research, 2002, vol. 8, pp. 1045-1050.
Koenig et al., "Biochemical basis for fluorouracil neurotoxicity", Archives of Neurology, 1970, vol. 23, pp. 155-160.
Kundu et al., "Studies of uracil derivatives and analogs. Syntheses of 5-(beta-trimethylsilyl)ethynyluracil and 5-ethynyluracil", Journal of Heterocyclic Chemistry, 1982, vol. 19, pp. 463-464.
Lemaire et al., "Cardiotoxicity of commercial 5-fluorouracil vials stems from the alkaline hydrolysis of this drug", British Journal of Cancer, 1992, vol. 66, pp. 119-127.
Lemaire et al., "Fluoroacetaldehyde as cardiotoxic impurity in fluorouracil (Roche)", The Lancet, 1991, vol. 337, pp. 560.
Levin et al., "Clinical development of eniluracil/fluourouracil: An oral treatment for patients with solid tumors", Investigational New Drugs, 2000, vol. 18, pp. 383-390.
Morrison et al., "Dihydropyrimidine dehydrogenase deficiency: A pharmacogenetic defect causing severe adverse reactions to 5-fluorouracil-based chemotherapy", Oncology Nursing Forum 24, 1997, vol. 24, pp. 83-88.
Myers et al., "The pharmacology of the fluoropyrimidines", Pharmacological Reviews, 1981, vol. 33, pp. 1-15.
Naguib et al., "Enzymes of uracil catabolism in normal and neoplastic human tissues", Cancer Research, 1985, vol. 45, pp. 5405-5412.
Ochoa et al., "Pharmacokinetics and bioequivalence of a combined oral formulation of eniluracil, an inactivator of dihydropyrimidine dehydrogenase, and 5-fluourouracil in patients with advanced solid malignancies", Annals of Oncology, 2000, vol. 11, pp. 1313-1322.
Okeda et al., "Experimental neurotoxicity of 5-fluorouracil and its derivatives is due to poisoning by the monofluorinated organic metabolites, monofluoroacetic acid and alpha-fluoro-beta-alanine", Acta Neuropathologica, 1990, vol. 81, pp. 66-73.
Paff et al., "Preclinical development of eniluracil: Enhancing the therapeutic index and dosing convenience of 5-fluorouracil", Investigational New Drugs, 2000, vol. 18, pp. 365-371.
Petit et al., "Circadian rhythm-varying plasma concentration of 5-fluourouracil during a five-day continuous venous infusion at a constant rate in cancer patients", Cancer Research, 1988, vol. 48, pp. 1676-1679.
Porter et al., "5-ethynyl-2(1H)-pyrimidinone: Aldehyde oxidase-activation to 5-ethynyluracil, a mechanism-based inactivator of dihydropyrimidine dehydrogenase", Biochemical Pharmacology, 1994, vol. 47, pp. 1165-1171.
Schilsky et al., "Phase I clinical and pharmacologic study of eniluracil plus fluorouracil in patients with advanced cancer", Journal of Clinical Oncology, 1998, vol. 16, pp. 1450-1457.
Schilsky et al., "Randomized, open-label, phase III study of a 28-day oral regimen of eniluracil plus fluorouracil versus intravenous fluorouracil plus leucovorin as first-line therapy in patients with metastatic/advanced colorectal cancer", Journal of Clinical Oncology, 2002, vol. 20, pp. 1519-1526.
Spector et al., "5-ethynyluracil (776C85): Inactivation of dihydropyrimidine dehydrogenase in vivo", Biochemical Pharmacology, 1993, vol. 46, pp. 2243-2248.
Spector et al., "Attenuation of the antitumor activity of 5-fluorouracil by (R)-5-fluoro-5,6-dihydrouracil", Cancer Research, 1995, vol. 55, pp. 1239-1241.
Heslin et al., "Dihydropyrimidine dehydrogenase (DPD) rapidly regenerates after inactivation by eniluracil (GW776C85) in primary and metastatic colorectal cancer", Cancer Chemother Pharmacol, 2003, pp. 399-404, vol. 52.
Mani et al., "Multicenter phase II study to evaluate a 28-day regimen of oral fluorouracil plus eniluracil in the treatment of patients with previously untreated metastatic colorectal cancer", Journal of Clinical Oncology, 2000, vol. 18, No. 15, pp. 2894-2901.
Goudgaon et al., "Phenylselenenyl- and Penylthio-substituted pyrimidines as inhibitors of dihydrouracil dehydrogenase and uridine phosphorylase", Journal of Medicinal Chemistry, 1993, vol. 36, pp. 4250-4254.
Lamont et al., "The oral fluoropyrimidines in cancer chemotherapy", Clinical Cancer Research, 1999, vol. 5, pp. 2289-2296.
Spector et al., "A possible cause and remedy for the clinical failure of 5-fluorouracil plus eniluracil", Clinical Colorectal Cancer, 2010, vol. 9, No. 1, pp. 52-54.
Meropol et al., "Phase II study of oral eniluracil, 5-fluorouracil, and leucovorin in patients with advanced colorectal carcinoma", Cancer, 2001, vol. 91, No. 7, pp. 1256-1263.
Yen-Revollo et al., "Can inhibiting dihydropyrimidine dehydrogenase limit hand-foot syndrome caused by fluoropyrimidines?", Clin Cancer Research, 2008, vol. 14, pp. 8-13.
Patent Cooperation Treaty, International Search Report, Application No. PCT/US2005/043706, 2006.
Patent Cooperation Treaty, International Search Report, Application No. PCT/US2010/052734, 2011.

* cited by examiner

Eniluracil
(5-Ethynyluracil)
(776C85)

5-Fluorouracil
(5-FU)

CHEMICAL STRUCTURES OF ENILURACIL AND 5-FU.

COMBINED ENILURACIL AND 5-FU TABLET.

THE BREAKDOWN (CATABOLIC) PATHWAY FOR 5-FU AND ITS BLOCKADE BY ENILURACIL.

METHODS FOR PREVENTING OR REDUCING NEUROTOXICITY ASSOCIATED WITH ADMINISTERING DPD INHIBITORS IN COMBINATION WITH 5-FU AND 5-FU PRODRUGS

CROSS-REFERENCE TO RELATED APPLICATION

This application claims the benefit under 35 U.S.C. §119 (e) of U.S. Provisional Patent Application No. 61/251,449, filed Oct. 14, 2009, where this provisional application is incorporated herein by reference in its entirety.

BACKGROUND OF THE INVENTION

1. Field of the Invention

This invention relates generally to cancer therapy, and more particularly to methods for preventing or minimizing neurotoxicity associated with cancer therapy using DPD inhibitors in combination with 5-FU and/or 5-FU prodrugs.

2. Description of the Related Art

5-Fluorouracil (5-FU) has been clinically used to treat solid tumors in cancer patients for over three decades (Ansfield et al., Cancer 39: 34-40, 1977; Grem et al., Cancer Treat Rep 71: 1249-1264, 1987; Chabner et al., Cancer, Principles and Practice of Oncology, 2nd Ed, pp 287-328 Philadelphia, Pa.: J B Lippincott Co, 1985). 5-FU must be activated by metabolic conversion to fraudulent uridine nucleotides (e.g., FUMP, FUDP, FUTP) and deoxyuridine nucleotides (e.g., FdUMP, FdUDP, FdUTP) that interfere with DNA synthesis and RNA functions (reviewed in Meyers, Pharmacol Rev, 33: 1-15, 1981; Dasher et al., Pharmac Ther 48: 189-222, 1990). Because 5-FU differs from uracil, its natural counterpart, by only a fluorine substitution in the 5-position, it is readily activated in cancer patients. Unfortunately, its structural similarity to uracil also accounts for its rapid and extensive conversion to products that have no antitumor activity. This metabolic process is referred to as catabolism. 5-FU is rapidly catabolized by the enzyme dihydropyrimidine dehydrogenase (DPD: EC 1312, uracil reductase) (Meyers, Pharmacol Rev, 33: 1-15, 1981; Dasher et al., Pharmac Ther 48: 189-222, 1990). Therefore, the antitumor efficacy of 5-FU for treating cancer relies on the delicate balance between metabolic conversion to antitumor nucleotides (activation) and metabolic conversion to useless metabolites (catabolism).

Furthermore, several clinical issues arise due to the metabolic catabolism of 5-FU. Firstly, because the levels of DPD vary among individuals (Fleming et al., Cancer Res 52: 2899-2902, 1992; Grem et al., Cancer Chemother Pharmacol 40: 117-125, 1997) and within individuals during the course of a day (Grem et al., Cancer Chemother Pharmacol 40: 117-125, 1997; Harris et al., Cancer Res 50: 197-201, 1990; Petit et al., Cancer Res 48: 1676-1679, 1988), the systemic levels of 5-FU or 5-FU generated from a prodrug produced from a given dose vary greatly, and therefore, render efficacy and toxicity highly unpredictable. At the extreme, patients genetically deficient in DPD experience severe and sometimes fatal toxicity when treated with 'standard' therapeutic doses of 5-FU (reviewed in Morrison et al., Oncol Nurs Forum 24: 83-88, 1997). Secondly, variable levels of gastro-intestinal DPD (Ho et al., Anticancer Res 6: 781-784, 1986; Naguib et al., Cancer Res 45: 5405-5412, 1985; Spector et al., Biochem Pharmacol 46: 2243-2248, 1993) create highly variable absorption of orally dosed 5-FU (Christophidis et al., Clin Pharmacokinetics 3: 330-336, 1978; Cohen et al., Cancer Chemother Rep 58: 723-731, 1974; Finch et al., Br J Clin Pharmacol 7: 613-617, 1979) that can result in unpredictable plasma levels of drug and produces undesirable toxicity or inadequate efficacy. Thirdly, tumors containing high levels of DPD are less likely to respond to 5-FU-treatment (Etienne et al., J Clin Oncol 13: 1663-1670, 1995; Fischel et al., Clin Cancer Res 1: 991-996, 1995).

Finally, the breakdown products of 5-FU, such as F-Bal, may produce neurotoxicity (Okeda et al., Acta Neuropathol 81: 66-73, 1990; Koenig et al. Arch Neurol 23: 155-160, 1970; Davis S T, et al. Biochem Pharmacol 1994; 48:233-6; reviewed in Saif M W, et al. Anticancer Drugs 2001; 12:525-31.), cardiotoxicity (et al., Lancet 337: 560, 1991; Lemaire et al., Br J Cancer 66: 119-127, 1992), palmer-plantarerythrodysaesthesia (hand-foot syndrome) (Hohneker, Oncology 12: 52-56, 1998), and GI toxicity (Spector et al., Cancer Res 55: 1239-1241, 1995) and appear to interfere with the antitumor activity (Spector et al., Cancer Res 55: 1239-1241, 1995; Cao, et al., Pharmacol 59: 953-960, 2000).

DPD is a ubiquitous enzyme that is the first and the rate-limiting step in the degradation (catabolism) of 5-FU. Studies have shown that inhibition of DPD greatly increases the half-life of 5-FU in plasma. Several DPD inhibitors have been studied, including those that irreversibly inactivate DPD as well as those that reversibly inhibit DPD. For example, eniluracil (5-ethynyluracil, 776C85) is a potent irreversible inactivator of DPD. Because DPD and the sequential enzymes in the catabolic pathway eventually convert 5-FU to α-fluoro-β-alanine (F-Bal) (reviewed in Spector et al., Drugs of The Future 1994; 19:565-71; Paff et al., Invest New Drugs 2000; 18:365-71), eniluracil converts the route of 5-FU elimination from catabolism to renal excretion, and, thereby increases the 5-FU elimination half-life from 10-20 min to 4.5-6.5 hr (Adjei et al., J Clin Oncol 2002; 20:1683-91; Ochoa et al., Ann Oncol 2000; 11:1313-22; Baker, Invest New Drugs 2000; 18:373-81; Baker et al., J Clin Oncol 1996; 14:3085-96; Guo et al., Cancer Chemother Pharmacol 2003; 52:79-85; Schilsky et al., J Clin Oncol 1998; 16:1450-7).

By preventing 5-FU breakdown in the gastrointestinal tract, eniluracil also enables 5-FU to be administered orally (Baker et al., J Clin Oncol 1996; 14:3085-96). In addition, eniluracil prevents the formation of 5-FU catabolites, such as F-Bal, that appear to be responsible for 5-FU-associated neurotoxicity (Davis et al., Biochem Pharmacol 1994; 48:233-6 reviewed in Saif M W, et al. Anticancer Drugs 2001; 12:525-31), and for hand-foot toxicity syndrome (Schilsky et al., J Clin Oncol 2002; 20:1519-26). In addition, 5-FU catabolites, such as F-Bal, appear to decrease the antitumor activity of 5-FU (Cao et al., Biochem Pharmacol 2000; 59:953-60; Spector T, et al. Cancer Res 1995; 55:1239-41 Spector et al., Drugs of The Future 1994; 19:565-71; Paff et al., Invest New Drugs 2000; 18:365-71).

Furthermore, because DPD is present in patients at different levels, the highly variable and nonlinear pharmacokinetics of 5-FU become highly predictable and linear when DPD is inactivated by eniluracil (reviewed in Baker, Invest New Drugs 2000; 18:373-81). Indeed, eniluracil significantly improved the antitumor efficacy of 5-FU and increased the therapeutic index in laboratory animals bearing tumors (Baccanari et al., Proc Natl Acad Sci USA 1993; 90:11064-812; Cao et al., Cancer Res 1994; 54:1507-10).

Eniluracil has been tested in Phase I clinical trials in cancer patients (reviewed in Levin et al., Invest New Drugs 18:383-90, 2000; Baker et al., J Clin Oncol 18: 915-926 2000; Schilsky et al., J Clin Oncol 4:1450-7, 1998). In these studies, eniluracil very potently eliminated DPD activity without causing toxicity. For example, a dose of 0.74 mg/m$^2$ (about 1 mg total) eliminated greater than 90% of DPD in peripheral blood cells for prolonged periods. The elimination half-life of 5-FU was increased from about 10 minutes to 3.5 hours by one dose of eniluracil. A dose of 3.7 mg/m² eniluracil increased the half-life of 5-FU to 4.5-6.5 hours. Higher doses added no apparent benefit.

Subsequently, two multicenter Phase III studies were conducted in patients with colorectal cancer using a combination pill containing eniluracil in ten-fold excess to 5-FU. Patients received 10 mg per square meter body surface area (mg/m²) eniluracil and 1 mg/m² 5-FU every 12 hr for 28 days. After one week off drug, the cycle was repeated. Although the results from the North American trial, where compliance was not a problem, showed encouraging antitumor activity, high tolerability, and minimal hand-foot syndrome, the regimen tended to produce less antitumor benefit than the standard regimen of 5-FU/leucovorin without eniluracil (Schilsky et al., J Clin Oncol 2002; 20:1519-26). An explanation of these results was not apparent at the time.

WO 2006/060697 describes the important finding that the antitumor activity of 5-FU is significantly diminished when excess eniluracil is present at the time 5-FU is administered to a subject. Therefore, to maximize the antitumor activity of 5-FU, low doses of eniluracil are proposed to be administered well before 5-FU such that at the time of 5-FU administration, 5-FU should be present in substantial excess to eniluracil. Otherwise, the antitumor efficacy of the 5-FU may be compromised. These results provide an explanation for the less than expected antitumor activity in the Phase III trials where the eniluracil ratio to 5-FU was 10:1 when 5-FU was administered.

Therefore, a clinical trial was initiated wherein cancer patients were administered a 5 mg dose of eniluracil followed by 5-FU at a 30-160 mg dose 12-24 hours later. Unexpectedly, the majority of the 41 patients undergoing this treatment experienced some form of mild to severe neurotoxicity, with the main neurological symptoms being ataxia (an unsteady gait), neuropathy, confusion, dizziness, and slurred speech.

Clearly, there remains an important and unmet need in the art for identifying optimal dosing and administration schedules for DPD inhibitors used in combination with 5-FU and 5-FU prodrugs in order to prevent or minimize neurotoxicity, to maximize the antitumor efficacy and therapeutic index of 5-FU and 5-FU prodrugs, to improve the predictability of dosing and to enable 5-FU and 5-FU prodrugs to be effectively dosed by oral administration. The present invention fulfills these needs and offers other related advantages.

SUMMARY OF THE INVENTION

Therefore, according to one aspect of the present invention, there is provided a method for preventing or minimizing neurotoxicity associated with treating a cancer patient with a combination comprising a DPD inhibitor and an anticancer agent selected from 5-FU or a 5-FU prodrug, comprising first administering a DPD inhibitor at a dose sufficient to substantially eliminate DPD activity in both nervous and non-nervous tissues, and thereafter administering the 5-FU or 5-FU prodrug, wherein the 5-FU or 5-FU prodrug is administered at a dose such that the 5-FU or 5-FU generated from the 5-FU prodrug is present in the patient in substantial excess of the DPD inhibitor.

In one illustrative embodiment of this aspect of the invention, a DPD inhibitor is administered at a dose sufficient to substantially eliminate DPD activity in both nervous and non-nervous tissues in a patient, such as a dose from about 14-40 mg/m² or from about 15-40 mg/m² or from about 16-40 mg/m². In more specific embodiments, the dose of eniluracil is from about 14-30 mg/m² or from about 15-30 mg/m² or from about 16-30 mg/m². In still other specific embodiments, the dose of eniluracil is from about 14-21 mg/m² or from about 15-21 mg/m² or from about 16-21 mg/m².

In another illustrative embodiment, the 5-FU or 5-FU prodrug is administered about 11-16 hours after the DPD inhibitor is administered.

In yet another illustrative embodiment, the 5-FU or 5-FU prodrug is administered at a time when at least about 3-5 elimination half-lives for the DPD inhibitor have passed since the DPD inhibitor was administered.

In another illustrative embodiment, the DPD inhibitor is administered at a dose sufficient to reduce DPD activity in nervous and non-nervous tissue in the patient to less than 5% of baseline DPD activity in the patient.

In still another illustrative embodiment, the 5-FU or 5-FU prodrug is administered at a dose such that at its time of administration the 5-FU or 5-FU generated from a prodrug is present in the patient in at least 10-fold excess of the DPD inhibitor.

Exemplary 5-FU prodrugs for use in the present invention may include, but are not limited to, 5'-esters, including phosphate esters: consisting of 5-fluorouridine, 5-fluorocytidine, 5-fluoro-2-deoxyuridine, 5-fluoro-2-deoxycytidine, 5'-deoxy-4',5-fluorouridine, and 5-fluoroarabinosyluracil, 5'-Deoxy-5-fluorouridine, 1-(2-tetrahydrofuranyl)-5-fluorouracil, 1-$C_{1-8}$ alkylcarbamoyl-5-fluorouracil derivative, 1-(2-tetrahydrofuryl)-5-fluorouracil, 5'-deoxy-5-fluoro-N-[(pentyloxy)carbonyl]-cytidine (capecitabine), or a compound that is converted to 5-FU in vivo.

In one preferred embodiment, the anticancer agent employed in the methods of the invention is 5-FU or capecitabine.

Generally, the DPD inhibitors useful in the methods of the present invention include, but are not limited to, irreversible DPD inhibitors. For example, certain illustrative DPD inhibitors comprise a 5-substituted uracil compound or a prodrug thereof. In a more specific embodiment, the DPD inhibitor comprises a uracil compound substituted in the 5-position by a halogen atom, a $C_{2-4}$ alkenyl group, a $C_{2-4}$ alkenyl group substituted by halogen, a $C_{2-6}$ alkynyl group, a $C_{2-6}$ alkynyl group substituted by a halogen, a cyano group, a $C_{1-4}$ alkyl group or a $C_{1-4}$ alkyl group substituted by halogen. In another specific embodiment, the DPD inhibitor comprises a uracil compound selected from the group consisting of eniluracil, 5-prop-1-ynyluracil, 5-cyanouracil, 5-prop-1-ynyluracil, 5-bromoethynyluracil, 5-(1-chlorovinyl)uracil, 5-iodouracil, 5-(2-bromovinyl)uracil, (E)-5-(2-bromovinyl)uracil 5-hex-1-ynyluracil, 5-vinyluracil, 5-trifluorouracil, 5-bromouracil and 5-(2-bromo-1-chlorovinyl)uracil.

In one preferred embodiment of the invention, the DPD inhibitor is eniluracil or a prodrug thereof.

In another preferred embodiment, the DPD inhibitor is eniluracil and the anticancer agent is 5-FU.

In still another preferred embodiment, the DPD inhibitor is eniluracil and the anticancer agent is capecitabine.

In one illustrative embodiment, the DPD inhibitor is eniluracil, the anticancer agent is 5-FU, the eniluracil is administered at a dose between about 16-40 mg/m², or at another DPD inhibitor dose or range as described herein, and the 5-FU is administered about 11-16 hours thereafter at a dose between about 15-50 mg/m².

In another illustrative embodiment, the DPD inhibitor is eniluracil, the anticancer agent is a 5-FU prodrug, the eniluracil is administered at a dose between about 16-40 mg/m², or at another DPD inhibitor dose or range as described herein, and the 5-FU prodrug is administered about 11-16 hours thereafter at a dose between about 40-150 mg/m².

In another illustrative embodiment, the DPD inhibitor is eniluracil, the anticancer agent is 5-FU, the eniluracil is administered at a dose between about 16-40 mg/m², or at another DPD inhibitor dose or range as described herein, and the 5-FU is administered at a dose between about 15-50 mg/m² at a time when at least about 3-5 elimination half-lives of the eniluracil have passed since the eniluracil was administered.

In another illustrative embodiment, the DPD inhibitor is eniluracil, the anticancer agent is a 5-FU prodrug, the eniluracil is administered at a dose between about 16-40 mg/m², or at another DPD inhibitor dose or range as described herein, and the 5-FU prodrug is administered at a dose between about 40-150 mg/m² at a time when at least about 3-5 elimination half-lives of the eniluracil have passed since the eniluracil was administered.

In another illustrative embodiment, the DPD inhibitor is eniluracil, the anticancer agent is 5-FU, the eniluracil is administered at a dose sufficient to reduce DPD activity in nervous and non-nervous tissue in the patient to less than 5% of baseline DPD activity in the patient, and the 5-FU is administered about 11-16 hours thereafter at a dose between about 15-50 mg/m².

In another illustrative embodiment, the DPD inhibitor is eniluracil, the anticancer agent is a 5-FU prodrug, the eniluracil is administered at a dose sufficient to reduce DPD activity in nervous and non-nervous tissue in the patient to less than 5% of baseline DPD activity in the patient, and the 5-FU prodrug is administered about 11-16 hours thereafter at a dose between about 40-150 mg/m².

In another illustrative embodiment, the DPD inhibitor is eniluracil, the anticancer agent is 5-FU or a 5-FU prodrug, the eniluracil is administered at a dose between about 16-40 mg/m², or at another DPD inhibitor dose or range as described herein, and the 5-FU or 5-FU prodrug is administered about 11-16 hours thereafter at a dose such that the 5-FU or 5-FU generated from the 5-FU prodrug is present in the patient in at least 10-fold excess of the DPD inhibitor.

According to another aspect of the present invention, there is provided an oral pharmaceutical time-release formulation comprising a DPD inhibitor and 5-FU or a 5-FU prodrug, wherein following administration of the formulation to a patient the 5-FU or 5-FU prodrug is not substantially released until at least about 11-16 hours after the DPD inhibitor has been released and, wherein following its release the 5-FU or 5-FU generated from a prodrug is present in the patient in at least about 10-fold excess of the DPD inhibitor remaining in the patient.

These and other aspects of the invention will be apparent upon reference to the following detailed description and attached figures. Patent and other documents cited herein to more specifically set forth various aspects of this invention are hereby incorporated by reference in their entireties.

DETAILED DESCRIPTION OF THE INVENTION

Figure 1:
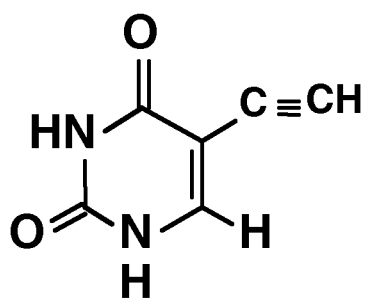
FIG. 1 shows the chemical structures of eniluracil and 5-FU.
Figure 1:
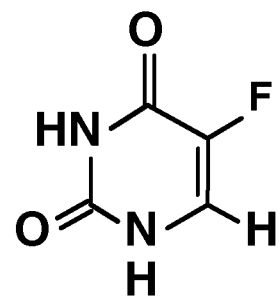

As described in WO2006/060697, DPD inhibitors such as eniluracil in excess ratios to 5-FU and 5-FU generated from prodrugs can compromise their antitumor activity, possibly by inhibiting one or more of the metabolic activating steps. Therefore, by ensuring that 5-FU or 5-FU generated from a prodrug levels are in sufficient excess of DPD inhibitor levels at the time the 5-FU or 5-FU prodrug is administered to a patient, the extent to which the DPD inhibitor may interfere with the antitumor activity of the 5-FU or 5-FU prodrug is advantageously minimized, and antitumor efficacy of these agents is thereby improved. Thus, an irreversible DPD inhibitor such as eniluracil should be dosed at the lowest dose that effectively inactivates DPD and sufficient time should lapse to allow extra DPD inhibitor not bound to DPD to be partially cleared such that at its time of administration the 5-FU is present in excess of the DPD inhibitor.

Based on this important finding, a clinical trial was initiated wherein cancer patients were administered a 5 mg dose of eniluracil, which was believed to be sufficient to systemically eliminate DPD activity in the patients. 5-FU was then administered 12-24 hours later at a dose of 30-160 mg. Unexpectedly, however, the majority of the 41 patients undergoing this treatment experienced some form of mild to severe neurotoxicity, with the main neurological symptoms being ataxia (an unsteady gait), neuropathy, confusion, dizziness, and slurred speech.

The present invention thus relates to methods by which this neurotoxicity can be prevented or minimized via proper selection of dosing and timing parameters to sufficiently eliminate DPD in both nervous and non-nervous tissues, while also ensuring that the 5-FU or 5-FU prodrug, at its time of administration, is in sufficient excess of any remaining DPD inhibitor so it will not interfere with the antitumor activity of the 5-FU or 5-FU generated from a prodrug.

The methods described herein are applicable to the treatment of essentially any cancer type in which 5-FU and/or 5-FU prodrugs have activity (e.g., any 5-FU-responsive cancer type or 5-FU prodrug-responsive cancer type), including, by way of illustration but not by way of limitation, breast cancer, lung cancer, colon cancer, pancreatic cancer, gastric cancer, bladder, renal cancer, head and neck cancer, esophageal cancer, hepatocellular cancer, and all malignant leukemias and lymphomas. Moreover, because the present invention improves the antitumor efficacy of 5-FU and 5-FU prodrugs, cancer types that may have shown less than desirable responsiveness to 5-FU previously may show improved responsiveness when administered according to the methods described herein.

It will be understood on the part of the skilled artisan, in view of this disclosure, that there exist a multitude of administration and dosing schedules that can be used in the methods described herein while ensuring that the DPD inhibitor is administered at a level sufficient to adequately inhibit DPD activity in both nervous and non-nervous tissues in the patient, while also ensuring that levels of the 5-FU or 5-FU prodrug at its time of administration are in a therapeutically effective amount and are in sufficient excess of DPD inhibitor level in the patient to minimize or eliminate inhibition of 5-FU antitumor activity. All such administration and dosing schedules are considered within the scope of the present invention.

In one illustrative embodiment of the invention, a DPD inhibitor is first administered (i.e., pre-dosed) to a patient in need thereof at a dose sufficient to substantially eliminate DPD activity in the patient in both nervous and non-nervous tissue, followed by administration of 5-FU or a 5-FU prodrug. By "substantially eliminate", it is meant that the level of DPD activity in both nervous and non-nervous tissues in the patient is reduced to less than 10%, and preferably to less than 5%, of the baseline level of DPD activity in the patient prior to administration of the DPD inhibitor. A baseline level of DPD activity for a patient can be readily determined in biological samples taken from a patient using known techniques (e.g., Baker et al., J Clin Oncol 18: 915-926 2000; Schilsky et al., J Clin Oncol 4:1450-7, 1998). However, it is now understood that assays of DPD inhibition in non-nervous tissues, such as circulating blood cells, may overestimate the degree of DPD inhibition in nervous tissues.

After first administering at least one DPD inhibitor, and thereby substantially eliminating DPD activity in the patient, in both nervous and non-nervous tissues, 5-FU or a 5-FU prodrug, or a combination thereof, is then administered to the patient after sufficient time has passed to allow the DPD inhibitor to be substantially, but not completely, cleared from the patient by elimination. In this respect, it may be desirable in certain embodiments that a low level of DPD inhibitor remain in the system leading up and/or during 5-FU administration in order to inactivate the activity of de novo synthesized DPD.

The delay in time between administration of the DPD inhibitor and the 5-FU or 5-FU prodrug can vary provided that upon administration of the 5-FU or 5-FU prodrug, it is present in the patient in substantial excess relative to the level of DPD inhibitor remaining in the patient at that time. In one illustrative embodiment, the 5-FU or 5-FU prodrug is administered at a dose such that the level of 5-FU or 5-FU generated from a prodrug is present in the patient at least in molar excess of the DPD inhibitor remaining in the patient, for example at least about 2-fold, at least about 3-fold, at least about 5-fold, at least about 10-fold, at least about 25-fold, at least about 50-fold, or at least about 100-fold excess relative to the level of DPD inhibitor remaining in the patient at the time the 5-FU or 5-FU prodrug is administered. The skilled artisan will recognize that any of a number of known and available techniques may be used for calculating and/or determining the level of excess of 5-FU or 5-FU generated from a prodrug in a patient relative to DPD inhibitor in accordance with the embodiments described herein. Such techniques may include, for example, HPLC, LC-MS, ELISA, and others. As noted above, it is believed that by ensuring that the 5-FU or 5-FU generated from a prodrug is present in sufficient excess relative to the level of DPD inhibitor in the patient at the time the 5-FU or 5-FU prodrug is administered, interference by the DPD inhibitor with the antitumor of the 5-FU or 5-FU prodrug is thereby minimized, and the efficacy of the 5-FU or 5-FU prodrug is thereby improved.

In further embodiments of the invention, the 5-FU or 5-FU prodrug is administered to the patient only after at least about 1, 2, 2.5, 3, 5, 7, 10, 14, or 21 elimination half-lives of the DPD inhibitor have passed since the DPD inhibitor was administered. The elimination half-lives for certain DPD inhibitors have been determined and, for those that have not, elimination half-lives can be readily determined using well known and established gas-chromatography/mass-spec and HPLC techniques (referenced in Baker et al., J Clin Oncol 18: 915-926 2000; Schilsky et al., J Clin Oncol 4:1450-7, 1998). The elimination half-life for eniluracil in humans has been reported to be about 3.5 hours (e.g., Baker et al., J Clin Oncol 18: 915-926 2000; Ochoa et al., Ann Oncol 11:1313-22, 2000), however it is possible that the half-life for DPD inhibitors may be dose-dependent and this dose dependency should be considered when determining an appropriate time delay between the administration of DPD inhibitor and 5-FU or 5-FU prodrug.

For certain embodiments of the invention that employ eniluracil as the DPD inhibitor, in order to allow the level of eniluracil to be sufficiently decreased by elimination prior to administration of the 5-FU or 5-FU prodrug, the 5-FU or 5-FU prodrug is administered at least about 3 hours, about 6 hours, about 8 hours, about 11 hours, about 16 hours, about 20 hours, about 36 hours, about 48 hours, or about 72 hours after administration of the eniluracil. In certain related embodiments of the present invention, the 5-FU or 5-FU prodrug is administered at a time between about 11-16 hours, about 8-20 hours, about 6-36 hours, about 3-48 hours, or about 3-72 hours after administration of the eniluracil. In still other embodiments of the invention, the 5-FU or 5-FU prodrug is not administered until, at its time of administration, the ratio of eniluracil to 5-FU in the patient, will be less than about 1:10, about 1:5, about 1:4, or about 1:3. Of course, it will be understood that these ranges and ratios are illustrative in nature and can be varied as necessary or desired for a particular dosing schedule provided that the presence of eniluracil is minimized or absent when 5-FU or 5-FU prodrug is dosed, and further provided that DPD activity has been substantially eliminated to a desired extent in both nervous and non-nervous tissue at the time the 5-FU or 5-FU prodrug is dosed.

The DPD inhibitor used according to the present invention is preferably one that irreversibly inactivates DPD. Thus, the inhibitor, such as eniluracil, will inactivate the enzyme and the extra inhibitor not covalently bound to the enzyme is partially cleared before 5-FU or a 5-FU prodrug is administered. Illustrative irreversible DPD inhibitors include, but are not limited to, DPD inhibitors comprising a 5-substituted uracil compound, or a prodrug thereof, particularly a uracil compound substituted in the 5-position by a halogen atom, a $C_{2-4}$ alkenyl group (e.g., vinyl) optionally substituted by halogen (e.g., 2-bromovinyl, 1-chlorovinyl or 2-bromo-1-chlorovinyl), a $C_{2-6}$ alkynyl group optionally substituted by a halogen atom, a cyano group, or a $C_{1-4}$ alkyl group substituted by halogen (e.g., trifluoromethyl).

In a more particular embodiment of the invention, the DPD inhibitor is selected from the group consisting of eniluracil, 5-prop-1-ynyluracil, 5-cyanouracil, 5-propynyluracil, 5-bromoethynyluracil, 5-(1-chlorovinyl)uracil, 5-iodouracil, 5-(1-bromovinyl)uracil, (E)-5-(2-bromovinyl)uracil, 5-hex-1-ynyluracil, 5-vinyluracil, 5-trifluorouracil, 5-bromouracil, and 5-(2-bromo-1-chlorovinyl)uracil, or a prodrug thereof.

In another illustrative embodiment, the DPD inhibitor is a prodrug of 5-bromovinyluracil, one illustrative compound being represented by the compound 1-β-D-arabinofuranosyl-(E)-5-(2-bromovinyl)uracil (also referred to as BV-araU or sorivudine). Certain illustrative prodrug compounds in this regard are described, for example, in U.S. Pat. No. 4,386,076, the disclosure of which is incorporated herein by reference.

In one preferred embodiment of the invention, the DPD inhibitor is eniluracil or a prodrug of eniluracil, such as 5-ethynyl-2(1H)-pyrimidinone (eniluracil missing the 4-oxygen) (Porter, et al., Biochem. Pharmacol 47: 1165-1171, 1994), a nucleoside or deoxynucleoside derivative of eniluracil, a compound that is converted to eniluracil in vivo, and/or a derivative of a DPD inactivator that is converted to the inactivator in vivo. By way of example, such compounds can include nucleoside derivatives which contain a nucleobase corresponding to the above 5-substituted uracil compounds, for example nucleoside derivatives containing a ribose, 2'-deoxyribose, 2',3'-dideoxyribose, arabinose or other cleavable sugar portion, which may additionally contain a 2'- or 3'-substituent such as a halogen or a 5' substituent such as an ester. More particular examples of such nucleoside derivatives include 1-(β-D-arabinofuranosyl)-5-prop-1-ynyluracil and 2',3'-dideoxy-5-ethynyl-3'-fluorouridine.

Numerous 5-FU prodrugs are known which may also be used in accordance with the present invention. A prodrug of 5-FU is a compound which is metabolized in vivo to 5-fluorouracil and may include, by way of illustration, 5-fluorouridine, 5-fluorocytidine, 5-fluoro-2-deoxyuridine, 5-fluoro-2-deoxycytidine, 5-fluoroarabinosyluracil, and their 5'-esters, including phosphate esters. Other illustrative compounds include 5'-deoxy-4',5-fluorouridine, 5'-deoxy-5-fluorouridine, 1-(2-tetrahydrofuranyl)-5-fluorouracil, a 1-$C_{1-8}$ alkyl-carbamoyl-5-fluorouracil derivative, 1-(2-tetrahydrofuryl)-5-fluorouracil, Ftorafur (Tegafur, an oral 5-FU prodrug that is widely used in Asian countries), and 5'-deoxy-5-fluoro-N-[(pentyloxy)carbonyl]-cytidine (capecitabine, marketed by Roche Laboratories Inc. as Xeloda®), or a compound that is converted to 5-FU in vivo.

It will be understood in view of this disclosure that the methods of the present invention can comprise administration schedules of whatever type, duration and dosing characteristics desired, provided the administration schedule is properly selected so that 5-FU-associated neurotoxicity is prevented or minimized and so that the 5-FU or 5-FU prodrug is present in sufficient excess of the level of DPD inhibitor remaining in the patient at the time the 5-FU or 5-FU prodrug is administered.

In certain particularly preferred embodiments of the present invention, the methods described herein employ the administration of the DPD inhibitor, eniluracil, in combination with 5-FU. For example, in exemplary embodiments, an administration schedule may be used which comprises a weekly or 5-day dosing schedule, where eniluracil is dosed the night before 5-FU and 5-FU is only dosed one day per week or once per day for 5 days.

It will be understood that suitable doses of eniluracil can vary provided that a sufficient amount is administered to a patient to substantially inhibit DPD activity in both nervous and non-nervous tissues, as described herein. In certain embodiments, for example, eniluracil is preferably administered at a dose from about 14-40 mg/$m^2$ or from about 15-40 mg/$m^2$ or from about 16-40 mg/$m^2$. In more specific embodiments, the dose of eniluracil is from about 14-30 mg/$m^2$ or from about 15-30 mg/$m^2$ or from about 16-30 mg/$m^2$. In still other specific embodiments, the dose of eniluracil is from about 14-21 mg/$m^2$ or from about 15-21 mg/$m^2$ or from about 16-21 mg/$m^2$ or from about 16-25 mg/$m^2$ or from about 12-35 mg/$m^2$. In still other embodiments of the invention, eniluracil can be dosed at about 14-50 mg/$m^2$, about 15-50 mg/$m^2$, about 16-50 mg/$m^2$, about 20-50 mg/$m^2$ or about 30-50 mg/$m^2$.

Of course, preferably, a DPD inhibitor dosage selected for administration to a patient according to the present invention is one that is at least sufficient to ensure that DPD activity in both nervous and non-nervous tissue of the patient is substantially eliminated. Moreover, it will be understood that any of the DPD inhibitor dose ranges described above, and elsewhere herein, may be used in the context of the various embodiments of the invention described herein.

In certain other embodiments of the invention, the 5-FU is administered about 11-16 hours after the eniluracil, thereby ensuring that the ratio of eniluracil to 5-FU will be considerably less than 1.0, as desired in order to avoid the decreased antitumor activity caused by high eniluracil to 5-FU ratios.

In other preferred embodiments, eniluracil is dosed at about 16-40 mg/$m^2$, or at another DPD inhibitor dose or range as described herein, and 5-FU is administered only after about 3-5 eniluracil elimination half-lives have passed.

In yet other preferred embodiments, eniluracil is dosed at about 16-40 mg/$m^2$, or at another DPD inhibitor dose or range as described herein, and 5-FU is administered only after sufficient time is allowed to pass such that, at the time of 5-FU administration, the ratio of eniluracil to 5-FU is ≤1:10.

Eniluracil doses of 14-21 mg/$m^2$ have been previously used (Schilsky et al., J Clin Oncol 1998; 16:1450-7; Baker et al., J Clin Oncol 2000; 18:915-26), however the eniluracil was administered one hour before, or simultaneously with the 5-FU dose. In contrast, the present invention uniquely doses eniluracil about 11-16 hours before 5-FU, in certain preferred embodiments, and employs doses of DPD inhibitor sufficient to inactivate DPD in both nervous tissue and non-nervous tissue, in order to avoid the unexpected neurotoxicity observed in human patients.

The amounts of eniluracil shown in Table 1 below may be used achieve doses in the 16-20 mg/$m^2$ range. The calculated amount of eniluracil remaining in the body after 10.5 hours (approximately three elimination half-lives) is also presented. Thus, if the weekly and the 5-day dosing schedules employ doses of 5-FU ranging between about 15-50 mg/$m^2$, the ratio of eniluracil to 5-FU will always be less than about 1:6 when 5-FU is administered. For example, when the commonly used 25 mg/$m^2$ dose of 5-FU is administered 10.5 hours after eniluracil, the ratio of eniluracil to 5-FU will be about 1:10 or less.

TABLE 1

The dose of eniluracil that delivers 16-20 mg/$m^2$ for patients of the indicated BSA, and the calculated amount of eniluracil remaining in the body after 10.5 hours (approximately three elimination half-lives).

| Patient's Body Surface Area (square meters) | Eniluracil Dose | | Estimated Amount of Eniluracil remaining 10.5 hr after dosing |
|---|---|---|---|
| ($m^2$) | (mg) | (mg/$m^2$) | (mg) |
| 1.3 | 25 | 19.2 | 3.1 |
| 1.4 | 25 | 17.9 | 3.1 |
| 1.5 | 30 | 20.0 | 3.8 |
| 1.6 | 30 | 18.8 | 3.8 |
| 1.7 | 30 | 17.6 | 3.8 |
| 1.8 | 30 | 16.7 | 3.8 |
| 1.9 | 30 | 15.8 | 3.8 |
| 2.0 | 40 | 20.0 | 5.0 |
| 2.1 | 40 | 19.0 | 5.0 |
| 2.2 | 40 | 18.2 | 5.0 |
| 2.3 | 40 | 17.4 | 5.0 |
| 2.4 | 40 | 16.7 | 5.0 |
| 2.5 | 50 | 20.0 | 6.3 |
| 2.6 | 50 | 19.2 | 6.3 |
| 2.7 | 50 | 18.5 | 6.3 |
| 2.8 | 50 | 17.9 | 6.3 |

For another example, if patients less than 1.9 $m^2$ received 30 mg eniluracil, and patients ≥1.9 $m^2$ received 45 mg eniluracil, these two doses would produce about 16-23 mg/$m^2$ over a wide range of body sizes. Furthermore, because eniluracil is nontoxic and has been shown to be safe when doses up to 50 mg per day for seven days (Schilsky et al., J Clin Oncol 4:1450-7, 1998), illustrative administration schemes can be simplified even further. For examples, if all patients were dosed with 40 mg eniluracil, the dosing range would encompass about 15-31 mg/$m^2$. In addition, if all patients received 50 mg eniluracil, the dosing range would be about 19-39 mg/$m^2$.

Accordingly, in other embodiments, an eniluracil dose range used according to the invention may advantageously comprise from about 16-23 mg/$m^2$, 15-31 mg/$m^2$, and 19-39 mg/$m^2$.

In still other embodiments of the invention, the time interval between administration of eniluracil and 5-FU can be between about 11-16 hours, about 8-20 hours, about 6-36 hours, about 3-48 hours, or about 3-72 hours.

In other embodiments, at least about 3-5, about 2.5-7, about 2-10, about 1-14, or 1-21 eniluracil elimination half-lives are allowed to pass before administration of 5-FU.

In further embodiments, eniluracil is administered the day before 5-FU is administered, or is administered on multiple days before 5-FU is administered.

In still other embodiments, 5-FU is administered at a dose of about 15-40 mg/m$^2$, 10-50 mg/m$^2$, 5-60 mg/m$^2$, or 5-70 mg/m$^2$ particularly for weekly and 5-day dosing schedules.

In still further embodiments, a 5-FU prodrug is administered at a dose of about 20-60 mg/m$^2$, 15-80 mg/m$^2$, 10-100 mg/m$^2$, or 5-150 mg/m$^2$ particularly for weekly and 5-day dosing schedules.

In additional embodiments, 5-FU is administered at a dose of about 0.8-1.2 mg/m$^2$ or 0.3-1.8 mg/m$^2$ every 8, 10, 12, 14, or 16 hours, particularly for prolonged therapy.

In still further embodiments of the present invention, the 5-FU administration schedule used according to the invention is a weekly schedule; a five-day schedule; a daily schedule; a daily schedule where 5-FU is dosed multiple times on a given day; a daily schedule where 5-FU is dosed for more than one day following the administration of eniluracil, which is dosed prior to 5-FU and on every day, every other day, or every third day during 5-FU therapy; a daily schedule where 5-FU is dosed multiple times on one or more days following the administration of eniluracil, which is dosed prior to 5-FU and on every day, every other day, or every third day during 5-FU therapy.

In one illustrative embodiment, eniluracil may be administered at a dose of about 16-40 mg/m$^2$, or at another DPD inhibitor dose range described herein, the night before 5-FU or, alternatively, can be administered in the morning followed by 5-FU administration in the evening. Using an illustrative dose for 5-FU of about 20 to 30 mg/m$^2$ for these schedules (Levin et al., Invest New Drugs 18:383-90, 2000; Schilsky et al., J Clin Oncol 4:1450-7, 1998; Guo et al., Cancer Chemother Pharmacol 52:79-85, 2003), for example, 5-FU should always be in substantial excess relative to eniluracil.

In another illustrative embodiment, a 28-day b.i.d. (twice daily for 28 days) schedule may be used. It will be understood that an administration schedule of this type will requires a different approach because 5-FU is dosed at only 1 mg/m$^2$ (see, e.g., Baker et al., J Clin Oncol 2000; 18:915-26). Thus, care must be taken to ensure that eniluracil is not present in excess of this low 5-FU dose. However, because high doses of eniluracil maintain DPD inactivated for extended periods, eniluracil could be dosed every 2, or possibly, every 3 days, for example. This strategy would ensure that, between eniluracil doses, the ratio of eniluracil to 5-FU will decrease with each subsequent dose of 5-FU.

In another illustrative embodiment, eniluracil (or another DPD inhibitor) is first administered and then multiple doses of 5-FU or 5-FU prodrug are thereafter administered at desired time points, before eniluracil is optionally administered again. For example, in an illustrative embodiment, eniluracil is first dosed and then multiple 5-FU doses are administered at illustrative time points of about 8, 10, 12, 14, or 16 hours thereafter, if desired, before eniluracil is optionally again administered and the cycle repeated.

The present invention includes as a further feature pharmaceutical formulations comprising at least one pharmaceutically acceptable carrier or excipient and further comprising a DPD inhibitor and/or 5-FU or a 5-FU prodrug, together in a single formulation or present as separate formulations to be administered at separate time points in accordance with the present invention. A carrier or excipient is "pharmaceutically acceptable" in the sense of being compatible with the other ingredients of the formulation and not injurious to the patient. Formulations include, for example, those adapted for oral, rectal, nasal, topical (including buccal and sublingual), vaginal and parenteral (including subcutaneous, intramuscular, intravenous and intradermal) administration. The formulations may conveniently be presented in unit dosage form and may be prepared by any methods well known in the pharmaceutical arts. Such methods include the step of bringing into association the active ingredient with the carrier that constitutes one or more accessory ingredients. In general, the formulations are prepared by uniformly and intimately bringing into association the active ingredient with liquid carriers or finely divided solid carriers or both, and then if necessary shaping the product.

Formulations according to the present invention may be prepared and/or administered using essentially any available technique. Formulations of the present invention adapted for oral administration, for example, may be presented as discrete units such as capsules, cachets or tablets each containing a predetermined amount of an active ingredient; as a powder or granules; as a solution or a suspension in an aqueous or non-aqueous liquid; or as an oil-in-water liquid emulsion or a water-in-oil liquid emulsion. An active ingredient may also be presented as a bolus, electuary or paste. Oral administration will typically be a preferred route of administration.

A tablet may be made, for example, by compression or molding, optionally with one or more accessory ingredients. Compressed tablets may be prepared by compressing in a suitable machine the active ingredient in a free-flowing form such as a powder or granules, optionally mixed with a binder (e.g., povidone, gelatin, hydroxypropylmethylcellulose), lubricant, inert diluent, preservative, disintegrant (e.g., sodium starch glycollate, cross-linked povidone, cross-linked sodium carboxymethylcellulose) surface-active or dispersing agent. Molded tablets may be made by molding in a suitable machine a mixture of the powdered compound moistened with an inert liquid diluent. The tablets may optionally be coated or scored and may be formulated so as to provide controlled release of the active ingredient therein using, for example, hydroxypropylmethylcellulose in varying proportions to provide the desired release profile.

Formulations for topical administration in the mouth, for example, include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier. Formulations for rectal administration, for example, may be presented as a suppository with a suitable base comprising for example cocoa butter or a salicylate. Formulation for vaginal administration, for example, may be presented as pessaries, tampons, creams, gels, pastes, foams or spray formulations containing in addition to the active ingredient such carriers as are known in the art to be appropriate.

Formulations for parenteral administration, for example, include aqueous and non-aqueous isotonic sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Typically, liquid formulations including one or more active agents are preferably buffered to a pH of 7 to 11, generally 9.5 to 10.5. Certain unit dosage formulations may include those containing a daily dose or unit, daily sub-dose, as hereinabove recited, or an appropriate fraction thereof, of an active ingredient.

Methods for making DPD inhibitors and 5-FU prodrugs described herein are known and may be carried out using conventional methodology. For example, DPD inhibitors referred to above may be prepared by the methods described in Heterocycl. Chem. 19(3) 463-4 (1982) for the preparation of 5-ethynyluracil; J. Chem. Soc. Perkin Trans. 1(16), 1665-70 (1981) for the preparation of 5-(2-bromovinyl)uracil, 5-bromoethynyluracil and 5-(2-bromo-1-chlorovinyl)uracil; Nucleic Acid Chemistry, Vol. 2, 927-30 (1978) for the preparation 5-cyano-uracil; Nucleic Acids Research, 1 (1) 105-7 (1974) for the preparation of 5-vinyluracil; Z. Chern 17(11) 415-16 (1977) for the preparation of 5-trifluoromethyluracil; Nucleic Acids Research 3 (10), 2845 (1976) for the preparation of 5-(1-chlorovinyl)uracil. Certain other compounds of the invention can be prepared in accordance with processes described in European Patent Specification No. 356166 for the preparation of 3'-fluoro-2',3'-dideoxy-5-alkynyluridine compounds, such as 2',3'-dideoxy-5-ethynyl-3'-fluorouridine, and European Patent Specification No. 272065 for the preparation of 5-alkynyluracil arabinosides, such as 1-(b-D-arabinofuranosyl)-5-prop-1-ynyluracil. These and other synthetic techniques are known and available for making compounds for use in the present invention.

Figure 2:
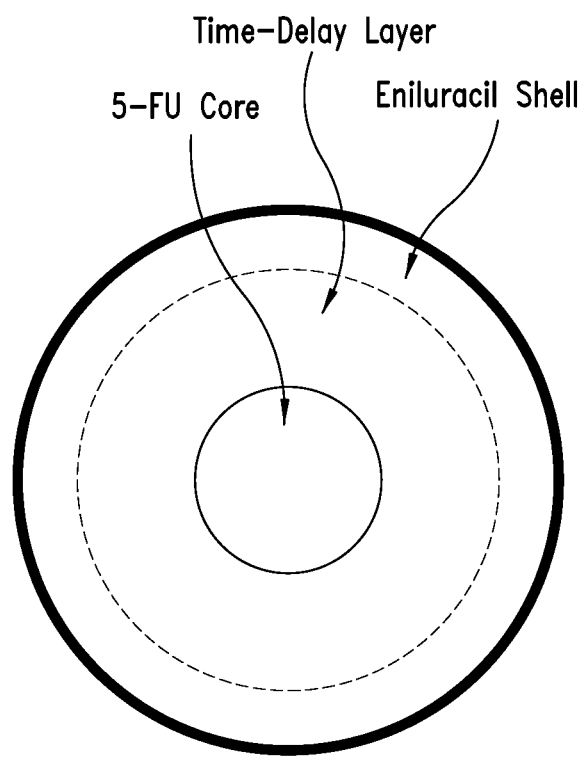
FIG. 2 shows an illustrative oral time-release formulation comprising eniluracil and 5-FU in a tablet form.

In one embodiment, the present invention provides a combination oral formulation in which a DPD inhibitor and 5-FU or a 5-FU prodrug are dosed together in a manner that allows for the desired temporal release of the components of the formulation into the patient within their desired dosage ranges. Differential time-release delivery of two components can be achieved using known techniques and materials. For example, in one embodiment, an oral formulation, e.g., in the form of a tablet, may be composed of three distinct layers, as depicted illustratively in FIG. 2. The outer layer can contain eniluracil in an immediate release formulation. The middle layer can be a time-release component (e.g., time-release buffer) that delays the release of 5-FU or 5-FU prodrug to a desired extent according to the present invention, which 5-FU or 5-FU prodrug is located in the core layer in an immediate release formulation. The DPD inhibitor and 5-FU or 5-FU prodrug are formulated in the proper doses and ratios described herein. In one preferred embodiment, the DPD inhibitor is eniluracil and the 5-FU or 5-FU prodrug is 5-FU or capecitabine.

In another embodiment, an alternative formulation can comprise known delivery vehicles, such as microspheres comprising 5-FU or 5-FU prodrug. In one embodiment, for example, 5-FU or 5-FU prodrug may be encapsulated within a shell of time-release component (e.g., time-release disintegrating buffer) and an outer layer providing immediate release of a DPD inhibitor. In one preferred embodiment, the DPD inhibitor is eniluracil and the 5-FU or 5-FU prodrug is 5-FU or capecitabine. These and other examples of illustrative combination formulations can be designed and made using known techniques to allow the appropriate time-delay between the delivery of the DPD inhibitor and the 5-FU or 5-FU prodrug in a single oral preparation.

In another embodiment, the methods described herein further comprise the administration of leucovorin. Leucovorin, or isovorin, the active isomer of leucovorin, is commonly used in conjunction with 5-FU for treating cancer patients. It may also be added to the above-described dosing regimens for eniluracil and 5-FU. Leucovorin has been shown to improve the antitumor efficacy of eniluracil and 5-FU in tumor-bearing rats and in tissue culture (Cao et al., Cancer Res 90:1507-1510, 1993; Fischel et al., Biochem Pharmacol 53: 1703-1709, 1997) and has been administered to patients receiving eniluracil and 5-FU (Schilsky et al., J Clin Oncol 4:1450-7, 1998; Guo et al., Cancer Chemother Pharmacol 52:79-85, 2003). Leucovorin is also advantageously available in an oral formulation.

The invention can be further understood upon consideration of the following non-limiting Example.

EXAMPLE

Example 1

Unexpected Neurotoxicity Associated with Administration of Eniluracil in Combination with 5-FU and Methods for Preventing or Minimizing the Same A clinical trial was initiated based on the important mechanistic findings described in WO 2006/060697. More specifically, cancer patients were administered a 5 mg dose of eniluracil and 12-24 hours thereafter were administered a 30-160 mg dose of 5-FU. Unexpectedly, however, the majority of the 41 patients undergoing this treatment experienced some form of mild to severe neurotoxicity, with the main neurological symptoms being ataxia (an unsteady gait), neuropathy, confusion, dizziness, and slurred speech.

Figure 3:
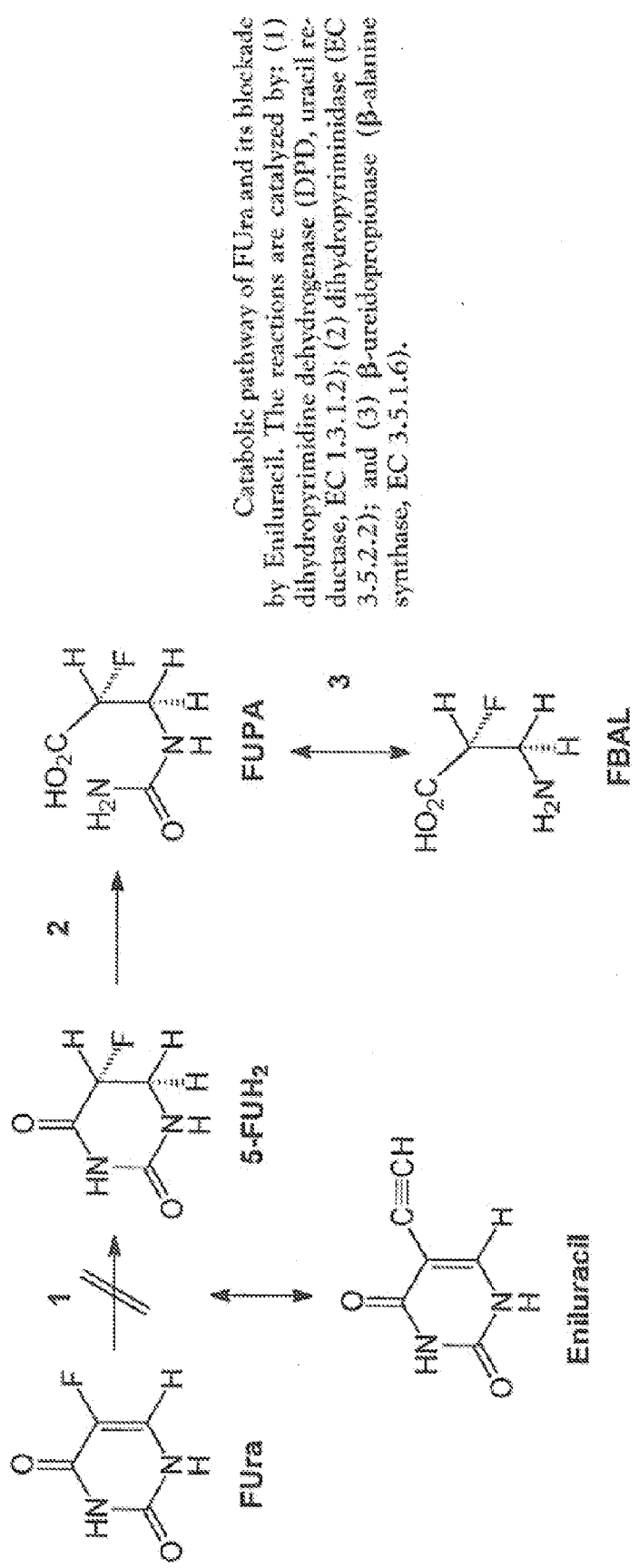
FIG. 3 shows the catabolic pathway for 5-FU and its blockade by eniluracil.

F-Bal is the dominant breakdown (catabolic) product of 5-FU. The pathway diagramed in FIG. 3 illustrates that DPD converts 5-FU to dihydrofluorouracil (5-FUH$_2$), which is converted to α-fluoro-β-ureidopropionic acid (FUPA) and then to F-Bal. Eniluracil blocks this pathway by inactivating DPD.

Although 5-FU itself does not cause neurotoxicity, and therefore was not directly responsible for the neurotoxicity observed in the clinical trial patients, studies have shown that one of the breakdown products of 5-FU, F-Bal, can cause neurotoxicity in mice, monkeys, cats, and dogs (Saif et al., Anticancer Drugs 2001; 12:525-31). In addition, studies in dogs have provided further evidence that F-Bal can cause neurotoxicity (Davis et al., Biochem Pharmacol 1994; 48:233-6). For example, intravenous administration of 5-FU to dogs achieved only low blood levels of 5-FU and induced seizures, muscle tremors, and ataxia. However, when dogs were pretreated with eniluracil, high blood levels of 5-FU were achievable without any neurotoxicity. Thus, by adequately blocking the catabolism of 5-FU in nervous tissue, eniluracil abrogated the neurotoxicity.

Because F-Bal appears to be the causative agent of 5-FU-associated neurotoxicity and eniluracil prevents the formation of F-Bal, the high prevalence of neurotoxicity in eniluracil-treated clinical trial patients was entirely unexpected, particularly given that the 5 mg dose of eniluracil used in the patients was believed to be sufficient to substantially eliminate their DPD, and therefore should have prevented the formation of the neurotoxic 5-FU catabolites in the nervous system.

However, upon analysis of the clinical trial data, and further in light what has been described in the scientific literature, it is now understood that although a particular dose of eniluracil may be sufficient to inactivate DPD in a patient's non-nervous tissues, such as circulating blood cells (Schilsky et al., J Clin Oncol 1998; 16:1450-7), it is not necessarily sufficient to adequately inactivate DPD in nervous tissues. For example, in rats, approximately six-fold higher doses of eniluracil are required to inactivate 50% of DPD in brain than are required to inactivate 50% of DPD in liver and other non-nervous tissues such as spleen, intestinal mucosa, and lung (Spector et al., Biochem Pharmacol 1993; 46:2243-8). Because the ability of eniluracil to access and inhibit the DPD enzyme in nervous tissues is somehow impeded, higher doses of eniluracil are required to inactivate DPD within nervous tissues than are required in non-nervous tissues. Accordingly, the dose of eniluracil used in the clinical trial appears to have been insufficient to inhibit DPD activity in human nervous tissues. Consequently, 5-FU appeared to be catabolized in the nervous tissues into neurotoxic catabolites, including F-Bal that produced neurotoxicity in the patients.

Furthermore, when 5-FU catabolism is inhibited in non-nervous tissues, 5-FU likely has greater access to nervous tissues. Consequently, if the dose of eniluracil is adequate to inhibit DPD in non-nervous tissues, but is too low to adequately inhibit DPD in nervous tissues, 5-FU will selectively be converted to F-Bal in nervous tissues. Therefore, doses of eniluracil that are sufficient to adequately inhibit DPD in non-nervous tissue, but not in nervous tissue, are likely to enable 5-FU-induced neurotoxicity.

This theory is strongly supported by the observation that the occurrence of neurotoxicity in patients decreased in those patient receiving higher doses of eniluracil. In the clinical trial where patients received 5 mg eniluracil before receiving 5-FU, the majority of the 41 patients experienced 5-FU-induced neurotoxicity. In contrast, for patients who received 20 mg eniluracil before receiving 5-FU, the incidence of neurotoxicity dropped to 2 out of 17 (12%) (Guo X D, et al. Cancer Chemother Pharmacol 2003; 52:79-85; Saif et al., Anticancer Drugs 2001; 12:525-31). It is particularly noteworthy that these two patients were large in size. Their body surface areas (BSA) were 2.1 $m^2$ and 2.5 $m^2$. Therefore, the 20 mg dose of eniluracil, delivered 9.5 mg/$m^2$ and 8.0 mg/$m^2$ eniluracil, respectively, to these patients. Importantly, the DPD in their peripheral blood cells was completely inactivated. Accordingly, based on this analysis, doses of eniluracil that are at least greater than 9.5 mg/$m^2$ appear to be necessary to ensure sufficient inactivation of DPD in nervous tissues to prevent neurotoxicity. Furthermore, eniluracil doses of about 11.5 mg/$m^2$ every 12 hours still result in a total incidence of severe neurotoxicity of 6% (Schilsky et al., J Clin Oncol 2002; 20:1519-26).

Thus, to avoid neurotoxicity in the clinic, it is critical that the dose of eniluracil be sufficiently high, preferably above about 12 mg/$m^2$ or 14 mg/$m^2$ or 15 mg/$m^2$ or 16 mg/$m^2$, and more preferably between about 12-21 mg/$m^2$ or 14-21 mg/$m^2$ or 15-21 mg/$m^2$ or 16-21 mg/$m^2$ or 16-25 mg/$m^2$ or 15-40 mg/$m^2$ or 16-40 mg/$m^2$, to inactivate DPD in both non-nervous tissues and nervous tissues. In addition, to maximize the antitumor activity of 5-FU, the 5-FU should be administered at a dose such that, at its time of administration, the ratio of eniluracil to 5-FU in the patent is preferably less than or equal to about 1:10, 1:5 or 1:3. However, it may be important that the level of eniluracil is not completely cleared when 5-FU is administered. In certain embodiments, for example, some eniluracil is preferably present to inactivate any newly synthesized DPD, which appears after eniluracil is eliminated (Spector T, et al. Biochem Pharmacol 1993; 46:2243-8; Heslin M J et al. Cancer Chemother Pharmacol 2003; 52:399-404: Keith B, et al. Clin Cancer Res 2002; 8:1045-50).

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method for minimizing neurotoxicity associated with treating a cancer patient with a combination comprising a DPD inhibitor and an anticancer agent selected from 5-FU or a 5-FU prodrug, comprising first administering a DPD inhibitor at a dose sufficient to substantially eliminate DPD activity in both nervous and non-nervous tissues, wherein the DPD inhibitor is eniluracil and is administered at a dose of 50 mg, and thereafter administering the 5-FU or 5-FU prodrug, wherein the 5-FU or 5-FU prodrug is administered at a dose such that the 5-FU or 5-FU generated from the 5-FU prodrug is present in the patient in at least 5-fold excess of the DPD inhibitor and at a time when 3-5 elimination half-lives for the DPD inhibitor have passed since the DPD inhibitor was administered.

2. The method of claim 1, wherein the 5-FU or 5-FU prodrug is administered about 11-16 hours after the DPD inhibitor is administered.

3. The method of claim 1, wherein the 5-FU or 5-FU prodrug is administered at a dose such that at its time of administration the 5-FU or 5-FU generated from a prodrug is present in the patient in at least 10-fold excess of the DPD inhibitor.

4. The method of claim 1, wherein the 5-FU prodrug is selected from the group consisting of 5-fluorouridine, 5-fluorocytidine, 5-fluoro-2-deoxyuridine, 5-fluoro-2-deoxycytidine, 5'-deoxy-4',5-fluorouridine, and 5-fluoroarabinosyluracil. 5'-Deoxy-5-fluorouridine, 1-(2-tetrahydrofuranyl)-5-fluorouracil, 1-$C_{1-8}$ alkylcarbamoyl-5-fluorouracil derivative, 1-(2-tetrahydrofuryl)-5-fluorouracil, and 5'-deoxy-5-fluoro-N-[(pentyloxy)carbonyl]-cytidine (capecitabine).

5. The method of claim 1, wherein the anticancer agent is 5-FU.

6. The method of claim 1, wherein the anticancer agent is capecitabine.

7. The method of claim 1, wherein the anticancer agent is 5-FU, and the 5-FU is administered about 11-16 hours thereafter at a dose between about 15-50 mg/$m^2$.

8. The method of claim 1, wherein the anticancer agent is a 5-FU prodrug, and the 5-FU prodrug is administered about 11-16 hours thereafter at a dose between about 40-150 mg/$m^2$.

9. The method of claim 8, wherein the 5-FU prodrug is capecitabine.

10. The method of claim 1, wherein the anticancer agent is 5-FU, and the 5-FU is administered at a dose between about 15-50 mg/$m^2$ at a time when 3-5 elimination half-lives of the eniluracil have passed since the eniluracil was administered.

11. The method of claim 1, wherein the anticancer agent is a 5-FU prodrug, and the 5-FU prodrug is administered at a dose between about 40-150 mg/$m^2$ at a time when 3-5 elimination half-lives of the eniluracil have passed since the eniluracil was administered.

12. The method of claim 11, wherein the 5-FU prodrug is capecitabine.

13. The method of claim 1, wherein the anticancer agent is 5-FU or a 5-FU prodrug, and the 5-FU or 5-FU prodrug is administered about 11-16 hours thereafter at a dose such that the 5-FU or 5-FU generated from the 5-FU prodrug is present in the patient in at least 10-fold excess of the DPD inhibitor.

14. A method for minimizing neurotoxicity associated with treating a cancer patient with a combination comprising a DPD inhibitor and an anticancer agent selected from 5-FU or a 5-FU prodrug, comprising first administering a DPD inhibitor at a dose sufficient to substantially eliminate DPD activity in both nervous and non-nervous tissues, wherein the DPD inhibitor is eniluracil and is administered at a dose of 20-50 mg/m$^2$, and thereafter administering the 5-FU or 5-FU prodrug, wherein the 5-FU or 5-FU prodrug is administered at a dose such that the 5-FU or 5-FU generated from the 5-FU prodrug is present in the patient in at least 5-fold excess of the DPD inhibitor and at a time when 3-5 elimination half-lives for the DPD inhibitor have passed since the DPD inhibitor was administered.

15. The method of claim 14, wherein the DPD inhibitor is administered at a dose from about 30-50 mg/m$^2$.

16. The method of claim 14, wherein the 5-FU or 5-FU prodrug is administered about 11-16 hours after the DPD inhibitor is administered.

17. The method of claim 14, wherein the 5-FU or 5-FU prodrug is administered at a dose such that at its time of administration the 5-FU or 5-FU generated from a prodrug is present in the patient in at least 10-fold excess of the DPD inhibitor.

18. The method of claim 14, wherein the 5-FU prodrug is selected from the group consisting of 5-fluorouridine, 5-fluorocytidine, 5-fluoro-2-deoxyuridine, 5-fluoro-2-deoxycytidine, 5'-deoxy-4',5-fluorouridine, and 5-fluoroarabinosyluracil. 5'-Deoxy-5-fluorouridine, 1-(2-tetrahydrofuranyl)-5-fluorouracil, 1-C$_{1-8}$ alkylcarbamoyl-5-fluorouracil derivative, 1-(2-tetrahydrofuryl)-5-fluorouracil, and 5'-deoxy-5-fluoro-N-[(pentyloxy)carbonyl]-cytidine (capecitabine).

19. The method of claim 14, wherein the anticancer agent is 5-FU.

20. The method of claim 14, wherein the anticancer agent is capecitabine.

21. The method of claim 14, wherein the anticancer agent is 5-FU, and the 5-FU is administered about 11-16 hours thereafter at a dose between about 15-50 mg/m$^2$.

22. The method of claim 14, wherein the anticancer agent is a 5-FU prodrug, and the 5-FU prodrug is administered about 11-16 hours thereafter at a dose between about 40-150 mg/m$^2$.

23. The method of claim 22, wherein the 5-FU prodrug is capecitabine.

24. The method of claim 14, wherein the anticancer agent is 5-FU, and the 5-FU is administered at a dose between about 15-50 mg/m$^2$ at a time when 3-5 elimination half-lives of the eniluracil have passed since the eniluracil was administered.

25. The method of claim 14, wherein the anticancer agent is a 5-FU prodrug, and the 5-FU prodrug is administered at a dose between about 40-150 mg/m$^2$ at a time when 3-5 elimination half-lives of the eniluracil have passed since the eniluracil was administered.

26. The method of claim 15, wherein the 5-FU prodrug is capecitabine.

27. The method of claim 14, wherein the anticancer agent is 5-FU or a 5-FU prodrug, and the 5-FU or 5-FU prodrug is administered about 11-16 hours thereafter at a dose such that the 5-FU or 5-FU generated from the 5-FU prodrug is present in the patient in at least 10-fold excess of the DPD inhibitor.

28. A method for minimizing neurotoxicity associated with treating a cancer patient with a combination comprising a DPD inhibitor and an anticancer agent selected from 5-FU or a 5-FU prodrug, wherein the cancer patient has a body surface area equal to or less than 2.3 m$^2$, the method comprising first administering a DPD inhibitor at a dose sufficient to substantially eliminate DPD activity in both nervous and non-nervous tissues, wherein the DPD inhibitor is eniluracil and is administered at a dose of 40 mg, and thereafter administering the 5-FU or 5-FU prodrug, wherein the 5-FU or 5-FU prodrug is administered at a dose such that the 5-FU or 5-FU generated from the 5-FU prodrug is present in the patient in at least 5-fold excess of the DPD inhibitor and at a time when 3-5 elimination half-lives for the DPD inhibitor have passed since the DPD inhibitor was administered.

29. The method of claim 18, wherein the 5-FU or 5-FU prodrug is administered about 11-16 hours after the DPD inhibitor is administered.

30. The method of claim 28, wherein the 5-FU or 5-FU prodrug is administered at a dose such that at its time of administration the 5-FU or 5-FU generated from a prodrug is present in the patient in at least 10-fold excess of the DPD inhibitor.

31. The method of claim 28, wherein the 5-FU prodrug is selected from the group consisting of 5-fluorouridine, 5-fluorocytidine, 5-fluoro-2-deoxyuridine, 5-fluoro-2-deoxycytidine, 5'-deoxy-4',5-fluorouridine, and 5-fluoroarabinosyluracil. 5'-Deoxy-5-fluorouridine, 1-(2-tetrahydrofuranyl)-5-fluorouracil, 1-C$_{1-8}$ alkylcarbamoyl-5-fluorouracil derivative, 1-(2-tetrahydrofuryl)-5-fluorouracil, and 5'-deoxy-5-fluoro-N-[(pentyloxy)carbonyl]-cytidine (capecitabine).

32. The method of claim 28, wherein the anticancer agent is 5-FU.

33. The method of claim 28, wherein the anticancer agent is capecitabine.

34. The method of claim 28, wherein the anticancer agent is 5-FU, and the 5-FU is administered about 11-16 hours thereafter at a dose between about 15-50 mg/m$^2$.

35. The method of claim 28, wherein the anticancer agent is a 5-FU prodrug, and the 5-FU prodrug is administered about 11-16 hours thereafter at a dose between about 40-150 mg/m$^2$.

36. The method of claim 35, wherein the 5-FU prodrug is capecitabine.

37. The method of claim 28, wherein the anticancer agent is 5-FU, and the 5-FU is administered at a dose between about 15-50 mg/m$^2$ at a time when 3-5 elimination half-lives of the eniluracil have passed since the eniluracil was administered.

38. The method of claim 28, wherein the anticancer agent is a 5-FU prodrug, and the 5-FU prodrug is administered at a dose between about 40-150 mg/m$^2$ at a time when 3-5 elimination half-lives of the eniluracil have passed since the eniluracil was administered.

39. The method of claim 30, wherein the 5-FU prodrug is capecitabine.

40. The method of claim 28, wherein the anticancer agent is 5-FU or a 5-FU prodrug, and the 5-FU or 5-FU prodrug is administered about 11-16 hours thereafter at a dose such that the 5-FU or 5-FU generated from the 5-FU prodrug is present in the patient in at least 10-fold excess of the DPD inhibitor.

* * * * *